US 7,022,867 B2

(12) United States Patent
Ueno et al.

(10) Patent No.: US 7,022,867 B2
(45) Date of Patent: Apr. 4, 2006

(54) SILICON COMPOUND AND METHOD FOR MAKING THE SAME

(75) Inventors: Kazunori Ueno, Ebina (JP); Yomishi Toshida, Yokohama (JP); Yuichi Hashimoto, Tokyo (JP); Akihiro Senoo, Tokyo (JP); Seiji Mashimo, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 738 days.

(21) Appl. No.: 10/243,768

(22) Filed: Sep. 16, 2002

(65) Prior Publication Data

US 2003/0216591 A1  Nov. 20, 2003

Related U.S. Application Data

(62) Division of application No. 09/078,565, filed on May 14, 1998, now Pat. No. 6,534,198.

(30) Foreign Application Priority Data

May 19, 1997 (JP) .............................. 1997/142956
Apr. 28, 1998 (JP) .............................. 1998/132635

(51) Int. Cl.
  *C07F 7/04* (2006.01)
  *C07F 7/08* (2006.01)
(52) U.S. Cl. ...................... 556/430; 556/413; 556/468; 556/476
(58) Field of Classification Search ................ 556/430, 556/413, 468, 479
See application file for complete search history.

(56) References Cited

U.S. PATENT DOCUMENTS

| | | | |
|---|---|---|---|
| 3,172,862 A | 3/1965 | Gurnee et al. | 252/301.3 |
| 3,173,050 A | 3/1965 | Gurnee | 313/108 |
| 3,220,972 A | 11/1965 | Lamoreaux | 260/46.5 |
| 3,710,167 A | 1/1973 | Dresner et al. | 313/108 A |
| 3,798,252 A | 3/1974 | Nitzsche et al. | 260/448.2 E |
| 4,292,434 A | 9/1981 | Lindner et al. | 556/479 |
| 4,356,429 A | 10/1982 | Tang | 313/503 |
| 4,539,507 A | 9/1985 | VanSlyke et al. | 313/504 |
| 4,720,432 A | 1/1988 | VanSlyke et al. | 428/457 |
| 5,220,181 A | 6/1993 | Kanai et al. | 257/40 |
| 5,362,559 A | 11/1994 | Hayase et al. | 428/333 |
| 5,407,987 A | 4/1995 | Fukushima et al. | 524/367 |
| 5,414,069 A | 5/1995 | Cumming et al. | 528/310 |
| 5,527,850 A | 6/1996 | Katayama et al. | 524/434 |
| 5,554,710 A | 9/1996 | Mori et al. | 528/32 |
| 5,830,972 A | 11/1998 | Ueda et al. | 528/38 |
| 5,958,609 A | 9/1999 | Ueda et al. | 428/690 |

FOREIGN PATENT DOCUMENTS

| | | |
|---|---|---|
| EP | 0 231 497 A1 | 8/1987 |
| EP | 0 786 924 A1 | 7/1997 |
| JP | 59-194393 | 11/1984 |
| JP | 2-272005 | 11/1990 |
| JP | 3-163188 | 7/1991 |
| JP | 3-180852 | 8/1991 |
| JP | 3-264692 | 11/1991 |
| WO | WO 95/00577 | * 1/1995 |

OTHER PUBLICATIONS van de Grampel et al., Silicon-containing Polymers Derived from mon and disubstituted cyclophosphazenes, Phosphorus, Sulfur and Silicon and the Related Elements, 1994, 93-94, 1-4, 273-276.*

Marc Lemmer et al., "Photoconductive Polysilanes Bearing Charge-Photogenerating Groups Based on Carbazole. 1 Synthesis via the Reductive Coupling of Diorganodichlorosilanes with Sodium," 8 *Polymers for Advanced Technologies* 116-124 (1997).

Shuzi Hayase, "Synthesis and Properties of Polysilanes Bearing Functional Substituents and Their Potential Applications," 3 *Trends in Polymer Science* 304-310 (1995).

Abstract of Japan, Pub. No. 03017131A, Pub. date Jan. 25, 1991; Applicant: Tonen Corp.; Inventor: Okumura Yoshiharu; Title: Production of Polysilanes.

Chihaya Adachi et al., "Organic Electroluminescent Device with a Three-Layer Structure," 27 (4) *Japan. J. Appl. Phys.* L713-L715 (Apr. 1988).

(Continued)

*Primary Examiner*—Johann Richter
*Assistant Examiner*—Chukwuma Nwaonicha
(74) *Attorney, Agent, or Firm*—Fitzpatrick, Cella, Harper & Scinto

(57) ABSTRACT

A silicon compound having a repeating unit represented by the following general formula (1):

$$\left( \begin{array}{c} R \\ | \\ Si \\ | \\ (CH_2)_m\text{—Ar} \end{array} \right)_n \quad (1)$$

wherein R is a hydrogen atom, a straight or branched alkyl group having 1 to 20 carbon atoms, a substituted or unsubstituted aryl group, or a substituted or unsubstituted heterocyclic group, Ar is a substituted or unsubstituted aryl group or an unsubstituted heterocyclic group, m is an integer of 2 or more, and n is an integer of 5,000 or less.

18 Claims, 3 Drawing Sheets

OTHER PUBLICATIONS

Chihaya Adachi et al., "Electroluminescence in Organic Films with Three-Layer Structure," 27(2) *Japan. J. Appl. Phys.* L269-L271 (Feb. 1988).

Hiroshi Ishiwara et al., "Lateral Solid Phase Epitaxy of Amorphous Si Films onto Nonplanar $SiO_2$ Patterns of Si Substrates," 48(12) *Appl. Phys. Lett.* 773-775 (Mar. 1986).

M. Pope et al., "Electroluminescence in Organic Crystals," 38 *J. Chem. Phys.* 2042-2043 (1963).

W. Helfrich et al., "Recombination radiation in Anthracene Crystals," 14(7) *Phys. Rev. Lett.* 229-231 (Feb. 1965).

C.W. Tang et al., "Organic Electroluminescent Diodes," 51(12) *Appl. Phys. Lett.* 913-915 (Sep. 1987).

W. Helfrich et al., "Transients of Volume-Controlled Current and of Recombination Radiation in Anthracene," 44(8) *J. Chem. Phys.* 2902-2909 (1966).

J. Kalinowski et al., "Magnetic Fields Effects on Recombination Radiation in Tetracene Crystal," 36(3) *Chem. Phys. Lett.* 345-348 (Nov. 1975).

R.H. Partridge, "Electroluminescence from Polyvinylcarbazole Films: 3. Electroluminescent Devices," 24 *Polymer* 748-754 (Jun. 1983).

P.S. Vincett et al., "Electrical Conduction and Low Voltage Blue Electroluminescence in Vacuum-Deposited Organic Films," 94 *Thin Solid Films* 171-183 (1982).

* cited by examiner

SILICON COMPOUND AND METHOD FOR MAKING THE SAME

This application is a division of application Ser. No. 09/078,565, filed May 14, 1998 now U.S. Pat. No. 6,534,198.

BACKGROUND OF THE INVENTION

1. Field of the Invention

The present invention relates to a novel silicon compound, a method for making the same, and an electroluminescent device using the same.

2. Description of the Related Art

High performance electronic devices require materials for effectively transporting only electrons or holes. Hole-transporting materials which transport only holes at a high efficiency have been widely used for electrophotographic photosensitive members and are expected as organic luminescent materials. For example, use of organic photoconductive (OPC) materials is rapidly spreading as photosensitive materials in electrophotography and the like. OPC materials have advantages in safety and productivity and costs compared to inorganic photosensitive materials, and have been vigorously used for copying machines and printers.

The OPC members generally have a multilayered structure of a charge generation layer (CGL) and a charge transport layer (CTL). The CTL is formed by coating a dispersion of a low molecule charge transport material (CTM), e.g. a triarylamine, hydrazone or dialkylaminobenzene derivative, in a transparent polymeric film, such as a polycarbonate resin. The concentration of the CTM in the polymer matrix is limited since the CTM crystal deposits at a high concentration. On the other hand, hole transferability decreases as the concentration decreases. Further, the CTL is fragile and has a low tensile strength. Such low mechanical strength causes scratches and cracks on the OPC member, resulting in image defects.

Exemplary polymeric charge transport materials are polystyrenes having hydrazone groups which are disclosed in Japanese Patent Laid-Open Nos. 2-272005 and 3-180852. These materials are formed into a film with great difficulty, and have unsatisfactory hole transport rates and residual potentials.

Pope et al., first discovered an electroluminescence (EL) of an organic material, that is, single-crystal anthracene in 1963 (*J. Chem. Phys.*, 38, 2042 (1963)). Helfinch and Schneider succeeded observation of relatively strong EL in an injection EL material containing a solution electrode system having a high injection efficiency in 1965 (*Phys. Rev. Lett.*, 14, 229 (1965)). Many studies of organic luminescent materials containing conjugated organic hosts and conjugated organic activators having fused benzene rings have been disclosed in U.S. Pat. Nos. 3,172,862, 3,173,050, and 3,710,167; *J. Chem. Phys.*, 44, 2902 (1966); *J. Chem. Phys.*, 58, 1542 (1973); and *Chem. Phys. Lett.*, 36, 345 (1975). Examples of disclosed organic hosts include naphthalene, anthracene, phenanthrene, tetracene, pyrene, benzpyrene, chrysene, picene, carbazole, fluorene, biphenyl, terphenyl, triphenylene oxide, dihalobiphenyl, trans-stilbene, and 1,4-diphenylbutadiene. Examples of disclosed activators include anthracene, tetracene and pentacene. Since these organic luminescent materials are provided as single layers having a thickness of more than 1 μm, a high electric field is required for luminescence. Under such a circumference, thin film devices formed by a vacuum deposition process have been proposed (for example, "Thin Solid Films" p. 171 (1982); *Polymer*, 24, 748 (1983); and *J. Appl. Phys.*, 25, L773 (1986)). Although the thin film devices are effective for reducing the driving voltage, their luminance is far from a level for practical use.

Tang et al. developed an EL device having a high luminance for a low driving voltage (*Appl. Phys. Lett.*, 51, 913 (1987) and U.S. Pat. No. 4,356,429). The EL device is fabricated by depositing two significantly thin layers, that is, a charge transport layer and a luminescent layer, between the positive electrode and the negative electrode by a vacuum deposition process. Such layered organic EL devices are disclosed in, for example, Japanese Patent Laid-Open Nos. 59-194393, 3-264692, and 3-163188, U.S. Pat. Nos. 4,539,507 and 4,720,432, and *Appl. Phys. Lett.*, 55, 1467 (1989).

Also, an EL device of a triple-layered structure having independently a carrier transport function and a luminescent function was disclosed in *Jpn. J. Apply. Phys.*, 27, L269 and L713 (1988). Since the carrier transportability is improved in such an EL device, the versatility of possible dyes in the luminescent layer is considerably increased. Further, the device configuration suggests feasibility of improved luminescence by effectively trapping holes and electrons (or excimers) in the central luminescent layer.

Monolithic organic EL devices are generally formed by vacuum deposition processes. EL devices having considerable luminance are also formed by casting processes (as described in, for example, Extended Abstracts (The 50th Autumn Meeting (1989), p. 1006 and The 51st Autumn Meeting (1990), p. 1041; The Japan Society of Applied Physics). Considerably high luminance is also achieved by a single-layered mixture-type EL device, in which the layer is formed by immersion-coating a solution containing polyvinyl carbazole as a hole transport compound, an oxadiazole derivative as a charge transport compound and coumarin-6 as a luminescent material (as described in Extended Abstracts (The 38th Spring Meeting (1991), p. 1086; The Japan Society of Applied Physics and Related Societies).

As described above, the organic EL devices have been significantly improved and have suggested feasibility of a wide variety of applications; however, these EL devices have some problems for practical use, for example, insufficient luminance, a change in luminance during use for a long period, and deterioration by atmospheric gas containing oxygen and humidity. Accordingly, a novel material not having such disadvantages and an electroluminescent device have been eagerly awaited.

SUMMARY OF THE INVENTION

It is an object of the present invention to provide a silicon compound having excellent charge transport characteristics and durability.

It is another object of the present invention to provide a silicon compound capable of easily forming a uniform film.

It is a further object of the present invention to provide an electroluminescent device emitting light with high luminance and a high efficiency and having high durability.

It is a still further object of the present invention to provide an electroluminescent device emitting light with a wide variety of wavelengths and hues.

It is another object of the present invention to provide an electroluminescent device easily produced at relatively low production costs and having a high degree of safety.

An aspect of the present invention is a silicon compound having a repeating unit represented by the following general formula (1):

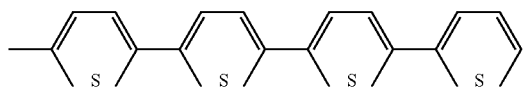

wherein R is a hydrogen atom, a straight or branched alkyl group having 1 to 20 carbon atoms, a substituted or unsubstituted aryl group, or a substituted or unsubstituted heterocyclic group, Ar is a substituted or unsubstituted aryl group or an unsubstituted heterocyclic group, m is an integer of 2 or more, and n is an integer of 5,000 or less.

Another aspect of the present invention is a method for synthesizing of a silicon compound having a repeating unit represented by the following general formula (1) by reacting a compound represented by the general formula (2) with a compound represented by the general formula (3):

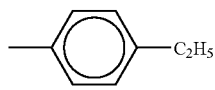

wherein R, Ar, m, and n are the same as above;

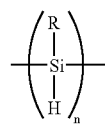 (2)

wherein R is a hydrogen atom, a straight or branched alkyl group having 1 to 20 carbon atoms, a substituted or unsubstituted aryl group, or a substituted or unsubstituted heterocyclic group, and n is an integer of 5,000 or less;

$$CH_2=CH-(CH_2)_{m-2}-Ar \quad (3)$$

wherein Ar is a substituted or unsubstituted aryl group or an unsubstituted heterocyclic group, and m is an integer of 2 or more.

A further aspect of the present invention is an electroluminescent device comprising a pair of electrodes and an organic compound layer interposed between said electrodes, said organic compound layer comprising a silicon compound having a repeating unit represented by the following general formula (1):

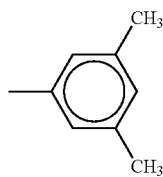

wherein R is a hydrogen atom, a straight or branched alkyl group having 1 to 20 carbon atoms, a substituted or unsubstituted aryl group, or a substituted or unsubstituted heterocyclic group, Ar is a substituted or unsubstituted aryl group or an unsubstituted heterocyclic group, m is an integer of 2 or more, and n is an integer of 5,000 or less.

The silicon compound in accordance with the present invention has excellent charge transport characteristics and can form a uniform and smooth film, hence it is useful as a charge transport material.

The method in accordance with the present invention enables ready production of the silicon compound.

The electroluminescent device in accordance with the present invention has high luminance at a low voltage for long periods, and can emit a variety of hues. For example, the electroluminescent device can emit primaries, i.e., red, blue and green; hence it can be used in displays. The device can be produced by a vacuum deposition or casting process at low production costs.

DESCRIPTION OF THE PREFERRED EMBODIMENT

Figure 1:
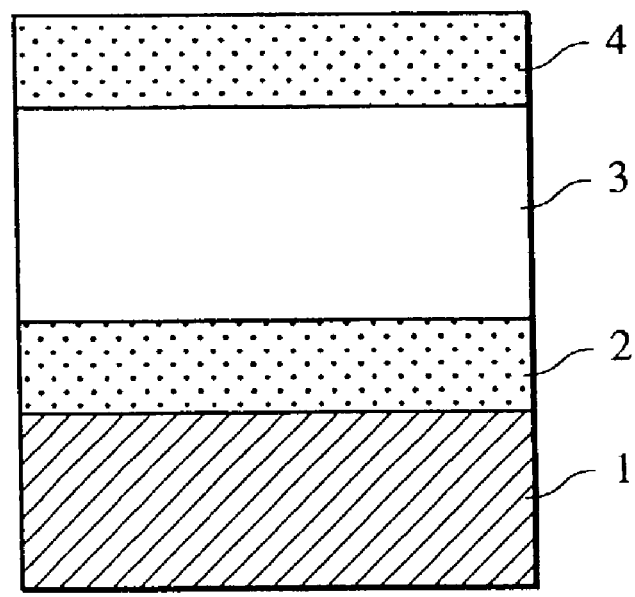
FIG. 1 is a schematic view of an embodiment of an electroluminescent device in accordance with the present invention.

The present inventors have studied intensively towards the resolution of problems caused by the charge transport material in the electroluminescent device, and have discovered that a silicon compound having a polysilane main chain and aryl groups has excellent charge transport characteristics and film formability and the resulting film has excellent stability. The present invention is completed under such findings.

The silicon compound in accordance with the present invention is represented by the following general formula (1):

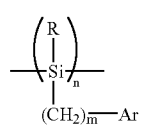 (1)

In the formula (1), R is a hydrogen atom, a straight or branched alkyl group having 1 to 20 carbon atoms and preferably 1 to 10, a substituted or unsubstituted aryl group, or a substituted or unsubstituted heterocyclic group. Examples of the straight or branched alkyl groups having 1 to 20 carbon atoms include straight alkyl groups, such as methyl, ethyl, propyl, hexyl and octyl groups, and branched alkyl groups, such as isopropyl and isobutyl groups.

Examples of unsubstituted aryl groups include polycyclic aryl groups, such as phenyl, biphenyl and terphenyl groups, and fused-ring aryl groups, such as naphthyl and anthranyl groups. Examples of unsubstituted heterocyclic groups include 6- and 5-membered rings, such as pyridyl, furyl, thienyl and pyrrolyl, and fused-ring heterocyclic groups such as acrydinyl. In the substituted aryl group and substituted heterocyclic group, each of the above-mentioned aryl and heterocyclic groups has a substituent group. Examples of the substituent groups include halogen atoms, e.g. chlorine and bromine; alkyl groups, e.g. methyl and ethyl groups; alkoxyl groups, e.g. methoxy and ethoxy groups; aryloxyl groups, e.g. a phenoxy group; primary and secondary amino groups; a nitro group; aryl groups, e.g. phenyl and tolyl groups; and aralkyl groups, e.g. benzyl and phenethyl groups.

In the formula (1), m is an integer of 2 or more and preferably 2 to 20, and n is an integer of 5,000 or less and preferably 30 to 1,000. Although the values of m and n are not limited to these ranges, these values are preferred in view of reactivity and yield in the production of the compound.

In the formula (1), Ar is a substituted or unsubstituted aryl group or an unsubstituted heterocyclic group. Examples of such groups are as follows:

(I) π-Conjugated Hydrocarbons having 12 or more Carbon Atoms:

Examples include polyphenyl groups, such as biphenyl, terphenyl and tetraphenyl, and stilbene groups, such as a naphthyl stilbene group.

(II) Fused-Ring Hydrocarbon Groups and Fused-Ring Heterocyclic Groups:

Examples of the fused-ring hydrocarbon groups include naphthyl, anthryl, pyrenyl, and fluorenyl groups. Examples of fused-ring heterocyclic groups include benzoxazolyl, dibenzofuryl, carbazolyl, and phenazone groups.

(III) Aromatic Polycyclic Groups:

Examples of the aromatic polycyclic groups include pyridyl, furyl, thienyl and pyrrolyl groups.

These groups (I) to (III) may have substituent groups. Examples of the substituent groups include halogen atoms, e.g. fluorine, chlorine, bromine and iodine; alkyl groups, e.g. methyl, ethyl, n-propyl and isopropyl; alkoxyl groups, e.g. methoxy, ethoxy and phenoxy; aralkyl groups, e.g. benzyl, phenethyl and propylphenyl; a nitro group; cyano groups; substituted amino groups, e.g. dimethylamino, dibenzylamino, diphenylamino, and morpholino; aryl groups, e.g. phenyl, tolyl, biphenyl, naphthyl, anthryl, and pyrenyl; and heterocyclic groups, e.g. pyridyl, thienyl, furyl, quinolyl, and carbazolyl.

(IV) Tertiary Amines each having a Substituted or Unsubstituted Arylene Group or Substituted or Unsubstituted Divalent Heterocyclic Group:

These groups are represented by the general formula (4):

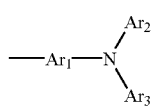

(4)

In the formula (4), $Ar_1$ represents a substituted or unsubstituted arylene group or a substituted or unsubstituted divalent heterocyclic group. Examples of the substituted or unsubstituted arylene group include phenylene, biphenylene and naphthylene groups. Examples of the substituted or unsubstituted divalent heterocyclic groups include divalent groups of pyridine, furan, and thiophene.

In the formula (4), $Ar_2$ and $Ar_3$ each represents a substituted or unsubstituted aryl group or a substituted or unsubstituted heterocyclic group. Examples of unsubstituted aryl groups include phenyl; polycyclic aryl groups, e.g. biphenyl and terphenyl groups; and fused-ring aryl groups, e.g. naphthyl and anthranyl groups. Examples of unsubstituted heterocyclic groups include 6- and 5-member heterocyclic groups, e.g. pyridyl, furyl, thienyl and pyrrolyl groups; and fused-ring heterocyclic groups, e.g. acrydinyl. In the substituted aryl group and substituted heterocyclic group, each of the above-mentioned aryl and heterocyclic groups has a substituent group. Examples of the substituent groups include halogen atoms, e.g. chlorine and bromine; alkyl groups, e.g. methyl and ethyl groups; alkoxyl groups, e.g. methoxy and ethoxy groups; aryloxyl groups, e.g. a phenoxy group; primary and secondary amino groups; a nitro group; aryl groups, e.g. phenyl and tolyl groups; aralkyl groups, e.g. benzyl and phenethyl groups; and alkenyl groups, e.g. formyl, acetyl and vinyl groups.

A silicon compound having the repeating unit of formula (1) is terminated by an appropriate terminal group. In general, the silicon compound is terminated with the group:

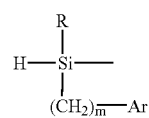

Accordingly, in a preferred embodiment the silicon compound of formula (1) has the formula:

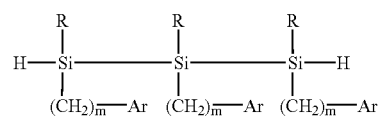

The silicon compound in accordance with the present invention represented by the formula (1) is synthesized by the reaction of a polysilane compound with a compound having any one of the groups (I) to (III). The reaction is preferably performed in the presence of a catalyst, such as platinum chloride acid hydrate.

The process of synthesis of the silicon compound is now described. The silicon compound represented by the formula (1) is synthesized by the reaction of a compound represented by the formula (2) with a compound represented by the formula (3):

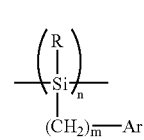

(1)

wherein R, Ar, m and n are the same as above;

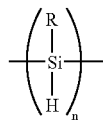 (2)

wherein R and n are the same as above; and

CH$_2$=CH—(CH$_2$)$_{m-2}$—Ar  (3)

wherein Ar and m are the same as above.

The molar ratio, the compound of the formula (2) : the compound of the formula (3), is preferably in a range of 1.0:10 to 10:1.0. It is preferable that the platinum chloride acid hydrate catalysis be added in an amount of 0.1 to 0.01 mole to 1 mole of the compound of the formula (2). Preferably, the reaction is performed in a solvent such as tetrahydrofuran at a temperature of 20 to 66° C. for a time of 3 to 10 hours.

Examples of the silicon compounds represented by the formula (1) will be described below without limiting the scope of the present invention.

| Compound | m | R | Ar |
|---|---|---|---|
| 1 | 2 | —CH$_3$ | —⟨phenyl⟩—⟨phenyl⟩ |
| 2 | 2 | —CH$_3$ | —⟨phenyl⟩—⟨phenyl⟩—⟨phenyl⟩ |
| 3 | 2 | —CH$_3$ | —⟨phenyl⟩—⟨phenyl(with phenyl substituent)⟩ |
| 4 | 2 | —CH$_3$ | —⟨phenyl⟩—⟨phenyl⟩—⟨phenyl⟩—⟨phenyl⟩ |
| 5 | 2 | —CH$_3$ | —⟨phenyl⟩—CH=CH—⟨phenyl⟩ |
| 6 | 2 | —CH$_3$ | —⟨phenyl⟩—CH=C(⟨phenyl⟩)$_2$ |
| 7 | 2 | —CH$_3$ | —⟨phenyl⟩—C(CH$_3$)=C(⟨phenyl⟩)$_2$ |
| 8 | 2 | —CH$_3$ | —⟨phenyl⟩—⟨phenyl⟩—CH=C(⟨phenyl⟩)$_2$ |

-continued

| | | | |
|---|---|---|---|
| 9 | 2 | —CH₃ | 4-phenyl-biphenyl-CH=C(phenyl)₂ |
| 10 | 2 | —CH₃ | biphenyl-phenyl-C(CH₃)₃ |
| 11 | 2 | —C₂H₅ | biphenyl |
| 12 | 2 | —C₂H₅ | terphenyl |
| 13 | 2 | —C₂H₅ | phenyl-CH=C(phenyl)₂ |
| 14 | 2 | -n-C₃H₇ | terphenyl |
| 15 | 2 | —CH(CH₃)₂ | biphenyl-CH=C(phenyl)₂ |
| 16 | 2 | —C₆H₁₃ | biphenyl-CH=C(phenyl)₂ |
| 17 | 2 | —C₈H₁₇ | biphenyl |
| 18 | 2 | —C₁₈H₃₇ | biphenyl-CH=C(phenyl)₂ |
| 19 | 2 | cyclohexyl (H) | quaterphenyl |

-continued

| | | | |
|---|---|---|---|
| 20 | 2 | cyclohexyl-H | biphenyl-CH=C(phenyl)₂ |
| 21 | 2 | phenyl | biphenyl |
| 22 | 2 | phenyl | phenyl-naphthyl |
| 23 | 2 | phenyl | terphenyl |
| 24 | 2 | phenyl | phenyl-CH=C(biphenyl)₂ |
| 25 | 2 | phenyl | naphthyl-CH=C(phenyl)₂ |
| 26 | 2 | -C₆H₄-CH₃ | 9,10-diphenylanthracene |
| 27 | 2 | -CH₂-phenyl | biphenyl-CH=C(phenyl)₂ |
| 28 | 3 | -CH₃ | terphenyl |

-continued
| 29 | 3 | —CH₃ | |
| 30 | 3 | —CH₃ | |
| 31 | 3 | —C₂H₅ | |
| 32 | 3 | —C₃H₇ | |
| 33 | 3 | | |
| 34 | 4 | —CH₃ | |
| 35 | 4 | —CH₃ | |
| 36 | 4 | —CH₃ | |
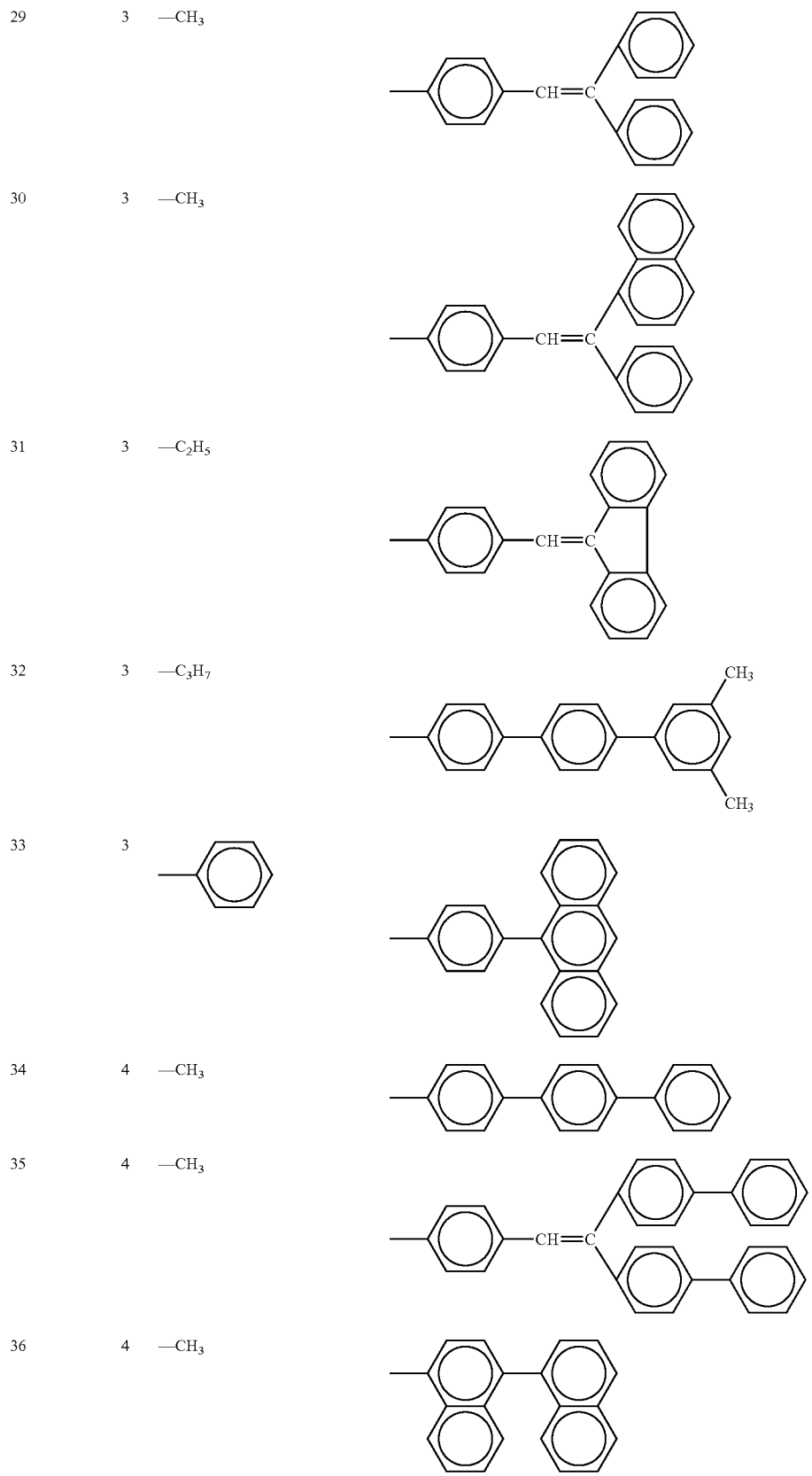

-continued
| | | | |
|---|---|---|---|
| 37 | 4 | —C₃H₇ | 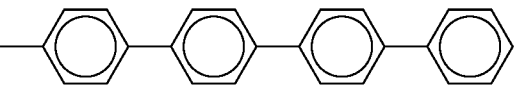 |
| 38 | 4 | —C₈H₁₇ | 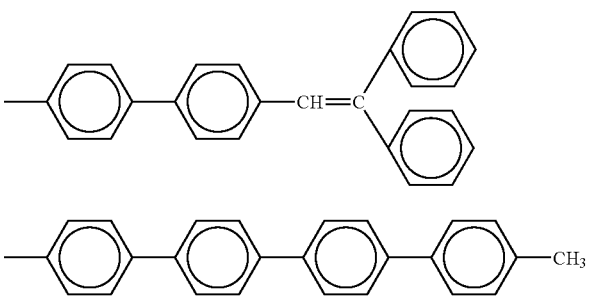 |
| 39 | 5 | —CH₃ | 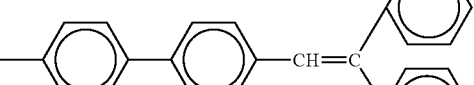 |
| 40 | 5 |  | 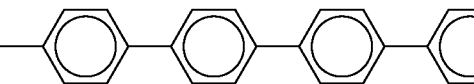 |
| 41 | 2 | —CH₃ |  |
| 42 | 2 | —CH₃ | 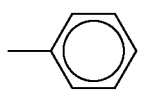 |
| 43 | 2 | —CH₃ |  |
| 44 | 2 | —CH₃ | 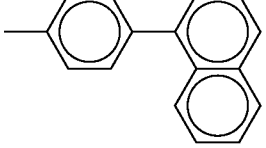 |

-continued
| | | | |
|---|---|---|---|
| 45 | 2 | —CH₃ | 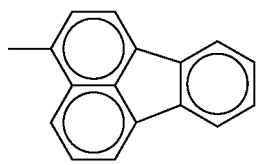 |
| 46 | 2 | —CH₃ | 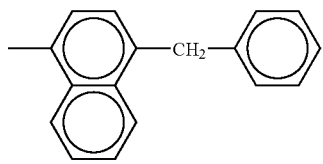 |
| 47 | 2 | —CH₃ | 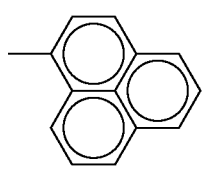 |
| 48 | 2 | —CH₃ | 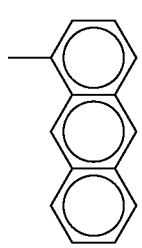 |
| 49 | 2 | —CH₃ | 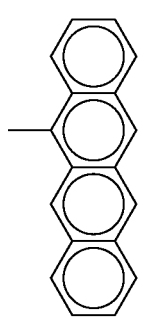 |
| 50 | 2 | —CH₃ | 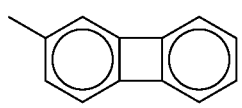 |
| 51 | 2 | —CH₃ | 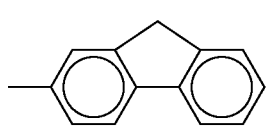 |
| 52 | 2 | —CH₃ | 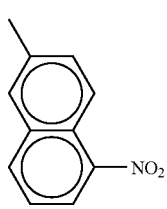 |

-continued
| 53 | 2 | —CH₃ | 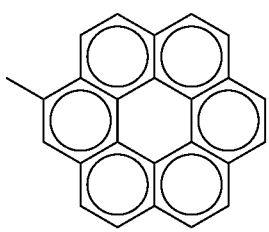 |
| 54 | 2 | —CH₃ | 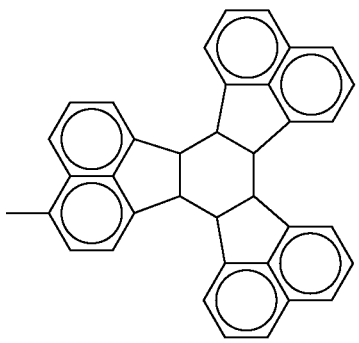 |
| 55 | 2 | —CH₃ | 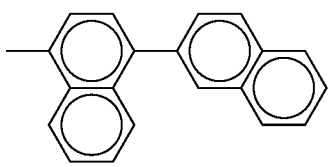 |
| 56 | 2 | —CH₃ | 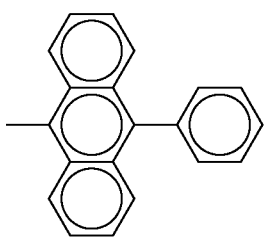 |
| 57 | 2 | —CH₃ | 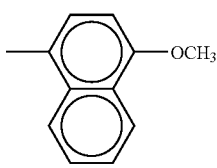 |
| 58 | 2 | —C₂H₅ | 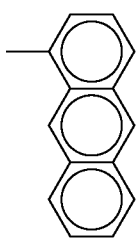 |
| 59 | 2 | —C₂H₅ | 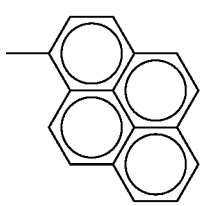 |

-continued
| | | | |
|---|---|---|---|
| 60 | 2 | —C$_2$H$_5$ | 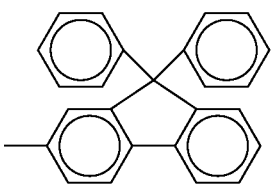 |
| 61 | 2 | —C$_2$H$_5$ | 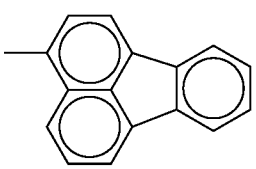 |
| 62 | 2 | —C$_3$H$_7$ | 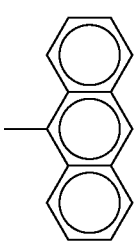 |
| 63 | 2 | —C$_3$H$_7$ | 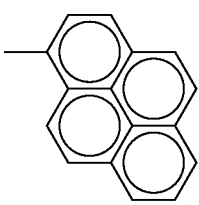 |
| 64 | 2 | —C$_3$H$_7$ | 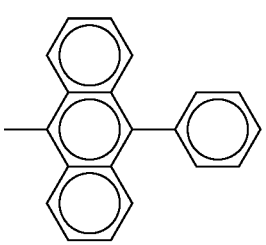 |
| 65 | 2 | 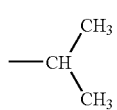 | 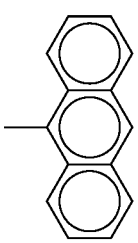 |
| 66 | 2 | 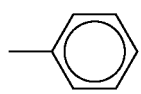 | 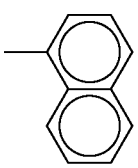 |

-continued
| | | | |
|---|---|---|---|
| 67 | 2 | 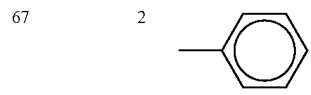 | 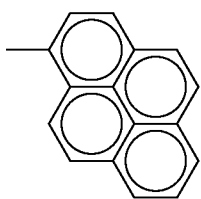 |
| 68 | 2 | 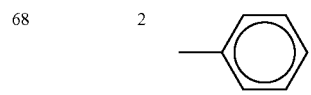 | 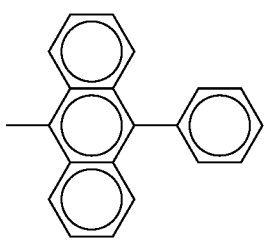 |
| 69 | 2 | 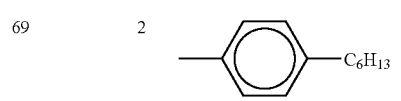 | 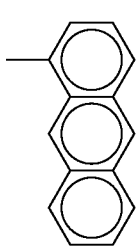 |
| 70 | 2 | 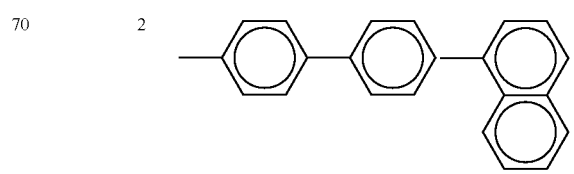 | |
| 71 | 3 | —CH$_3$ | 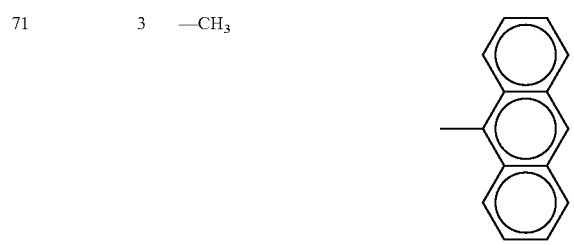 |
| 72 | 3 | —CH$_3$ | 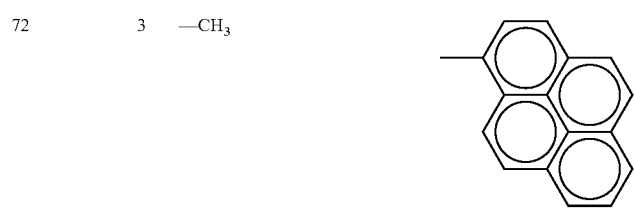 |
| 73 | 3 | —C$_3$H$_7$ | 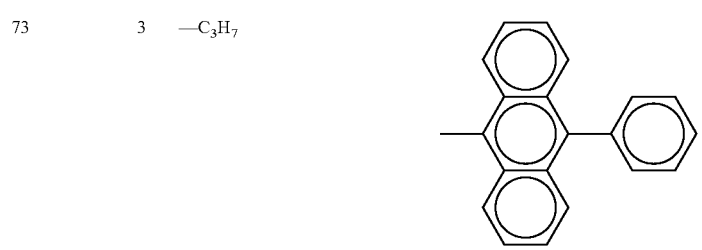 |

-continued
| | | | |
|---|---|---|---|
| 74 | 3 | —C$_8$H$_{17}$ | 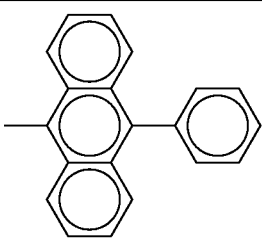 |
| 75 | 3 | 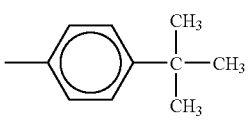 | 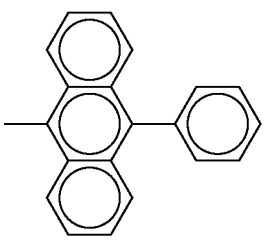 |
| 76 | 4 | —C$_2$H$_5$ | 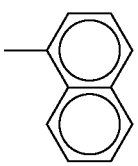 |
| 77 | 4 | —C$_8$H$_{17}$ | 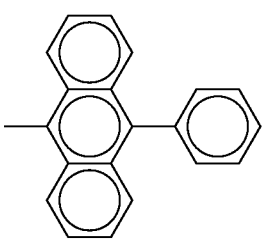 |
| 78 | 4 | 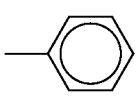 | 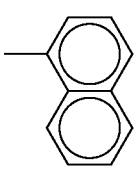 |
| 79 | 5 | —CH$_3$ | 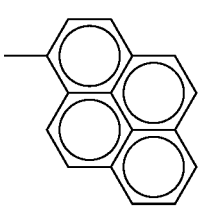 |
| 80 | 5 | —C$_2$H$_5$ | 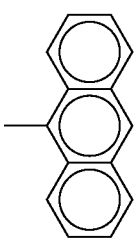 |
| 81 | 2 | —CH$_3$ | 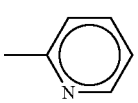 |

-continued

| | | | |
|---|---|---|---|
| 82 | 2 | —CH$_3$ | (2-methylpyran-yl) |
| 83 | 2 | —CH$_3$ | (2-thienyl-methyl) |
| 84 | 2 | —CH$_3$ | (N-methyl-dihydropyridinyl) |
| 85 | 2 | —CH$_3$ | (1,3,4-oxadiazolyl) |
| 86 | 2 | —CH$_3$ | (quinolinyl) |
| 87 | 2 | —CH$_3$ | (phenyl-oxadiazolyl) |
| 88 | 2 | —CH$_3$ | (dibenzofuranyl) |
| 89 | 2 | —CH$_3$ | (dibenzothiophenyl) |
| 90 | 2 | —CH$_3$ | (N-ethylcarbazolyl) |
| 91 | 2 | —CH$_3$ | (bithienyl) |
| 92 | 2 | —CH$_3$ | (quaterthienyl) |
| 93 | 2 | —CH$_3$ | (oligothienyl)$_3$ |

-continued
| | | | |
|---|---|---|---|
| 94 | 2 | —CH$_3$ | 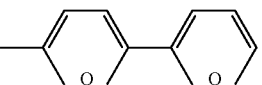 |
| 95 | 2 | —CH$_3$ | 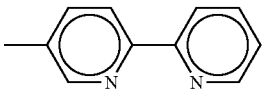 |
| 96 | 2 | —CH$_3$ | 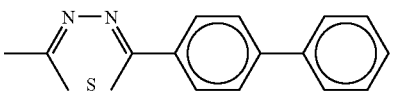 |
| 97 | 2 | —CH$_3$ | 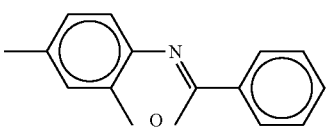 |
| 98 | 2 | —CH$_3$ | 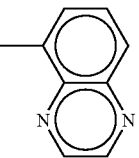 |
| 99 | 2 | —CH$_3$ | 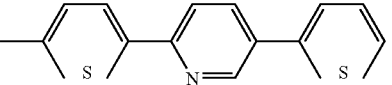 |
| 100 | 2 | —CH$_3$ | 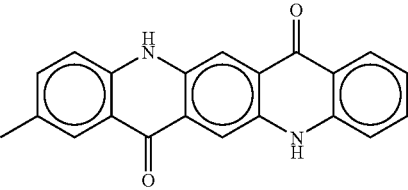 |
| 101 | 2 | —CH$_3$ | 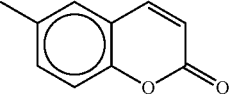 |
| 102 | 2 | —CH$_3$ | 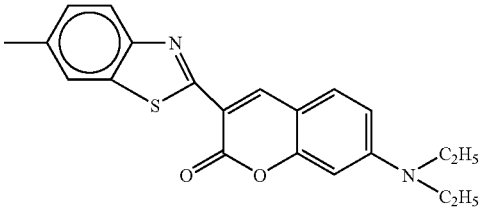 |
| 103 | 2 | —CH$_3$ | 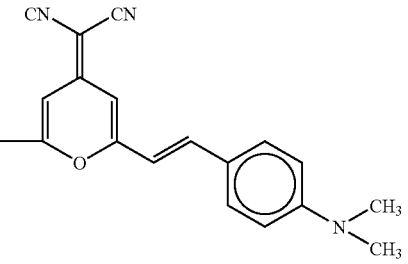 |

-continued
| | | | |
|---|---|---|---|
| 104 | 2 | —CH₃ | 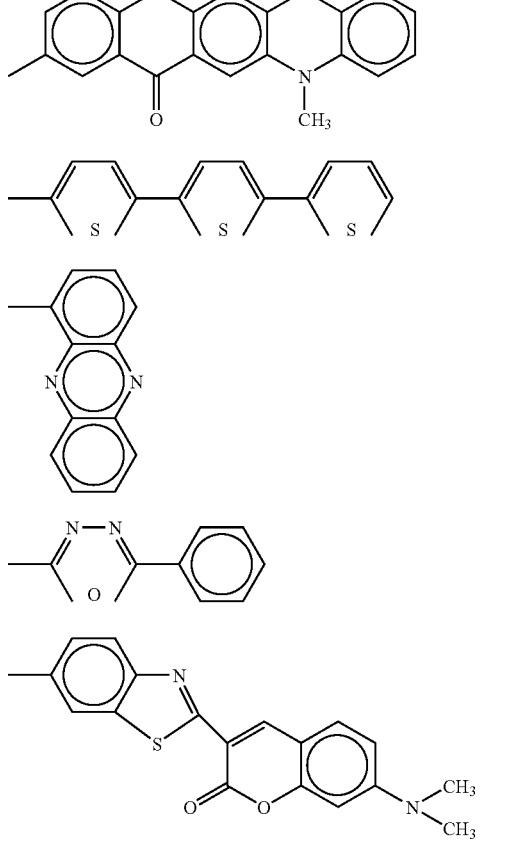 |
| 105 | 3 | —CH₃ | 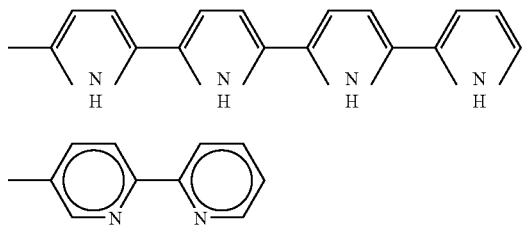 |
| 106 | 3 | —CH₃ | 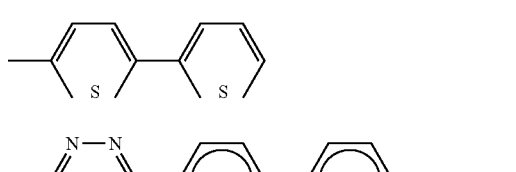 |
| 107 | 3 | —CH₃ |  |
| 108 | 3 | —C₂H₅ |  |
| 109 | 3 | —C₈H₁₇ | 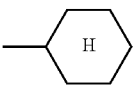 |
| 110 | 3 | 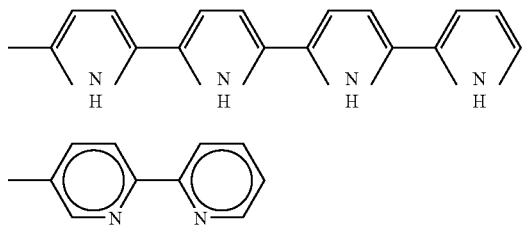 | 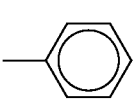 |
| 111 | 2 | 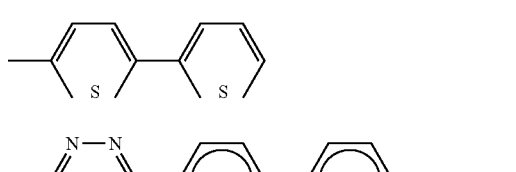 | 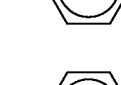 |
| 112 | 2 |  |  |
| 113 | 2 |  | |
| 114 | 2 | | |

| | | | |
|---|---|---|---|
| 115 | 2 | (p-tolyl) | (acetyl-S)N=N(p-tolyl-S) |
| 116 | 2 | —C$_3$H$_7$ | (tri-thiophene chain) |
| 117 | 2 | —C$_{18}$H$_{37}$ | (benzoxazole-phenyl) |
| 118 | 2 | —C$_8$H$_{17}$ | (bis-oxadiazole-phenylene) |
| 119 | 3 | Ph | (acetyl-O)N=N(phenyl) |
| 120 | 3 | (p-CN-phenyl) | (bi-thiophene) |

| Compound | m | R | Ar$_1$ | Ar$_2$ | Ar$_3$ |
|---|---|---|---|---|---|
| 121 | 2 | Ph | p-phenylene | Ph | Ph |
| 122 | 2 | Ph | p-phenylene | p-tolyl | p-tolyl |
| 123 | 2 | Ph | p-phenylene | p-C$_2$H$_5$-phenyl | p-C$_2$H$_5$-phenyl |
| 124 | 2 | Ph | p-phenylene | p-OCH$_3$-phenyl | p-OCH$_3$-phenyl |
| 125 | 2 | Ph | p-phenylene | p-tolyl | Ph |
| 126 | 2 | Ph | p-phenylene | p-Cl-phenyl | p-tolyl |
| 127 | 2 | Ph | p-phenylene | 3,4-dimethylphenyl | 3,4-dimethylphenyl |

-continued
| | | | | | |
|---|---|---|---|---|---|
| 128 | 2 | Ph |  | 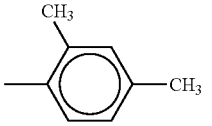 | 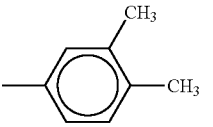 |
| 129 | 2 | Ph |  | 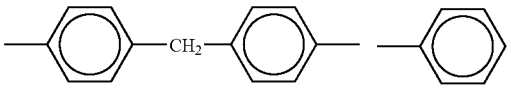 |  |
| 130 | 2 | Ph |  | 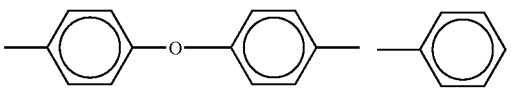 | 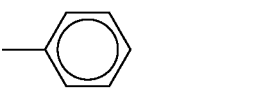 |
| 131 | 2 | CH$_3$ |  | 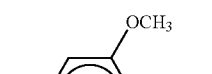 | 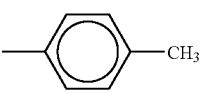 |
| 132 | 2 | CH$_3$ |  | 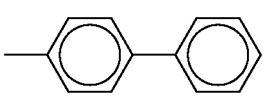 | 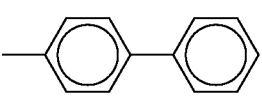 |
| 133 | 2 | CH$_3$ |  | 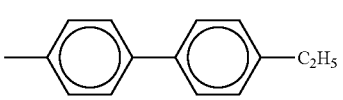 | 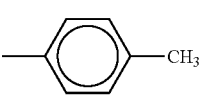 |
| 134 | 2 | CH$_3$ |  | 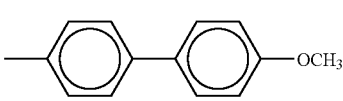 | 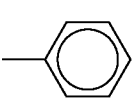 |
| 135 | 2 | CH$_3$ |  | 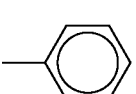 | 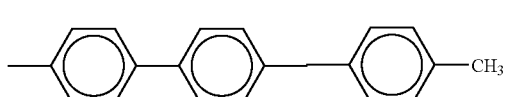 |
| 136 | 2 | CH$_3$ | 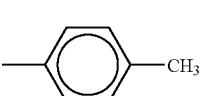 |  | 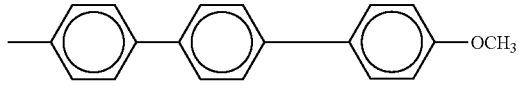 |
| 137 | 2 | CH$_3$ | 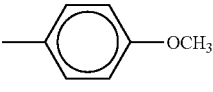 | 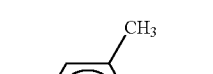 |  |
| 138 | 2 | CH$_3$ | 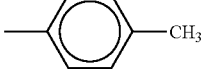 | 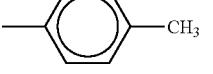 |  |
| 139 | 2 | CH$_3$ |  | 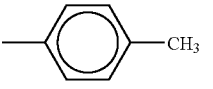 | 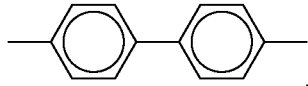 |
| 140 | 3 | CH$_3$ | 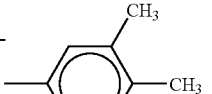 | 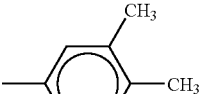 |  |
| 141 | 2 | CH$_3$ | 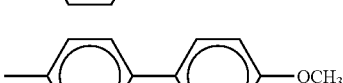 | 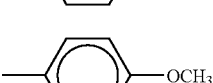 | |

-continued
| | | | | | |
|---|---|---|---|---|---|
| 142 | 3 | CH₃ | 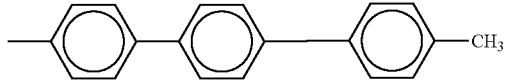 | |  |
| 143 | 3 | CH₃ | 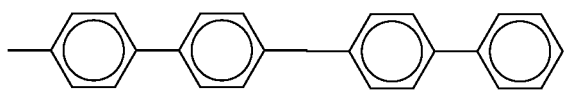 | | 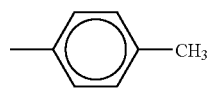 |
| 144 | 3 | CH₃ | 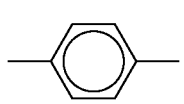 | 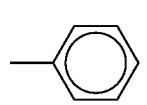 | 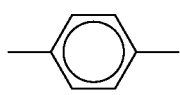 |
| 145 | 3 | CH₃ | 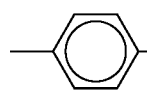 | 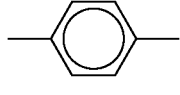 | 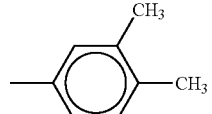 |
| 146 | 3 | CH₃ | 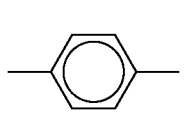 | 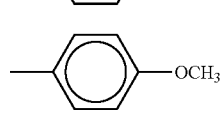 | 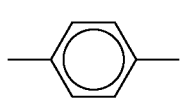 |
| 147 | 3 | CH₃ | 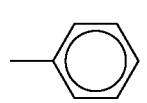 | 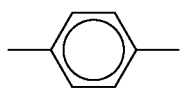 | 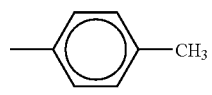 |
| 148 | 3 | CH₃ |  |  | 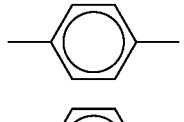 |
| 149 | 3 | CH₃ | 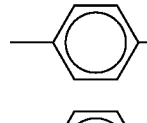 |  |  |
| 150 | 3 | CH₃ |  |  |  |
| 151 | 2 | Ph |  | 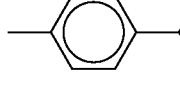 | 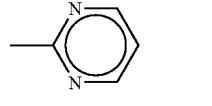 |
| 152 | 2 | Ph | | | |
| 153 | 2 | Ph | | | |
| 154 | 2 | Ph | | | |
| 155 | 2 | Ph | | | |

-continued

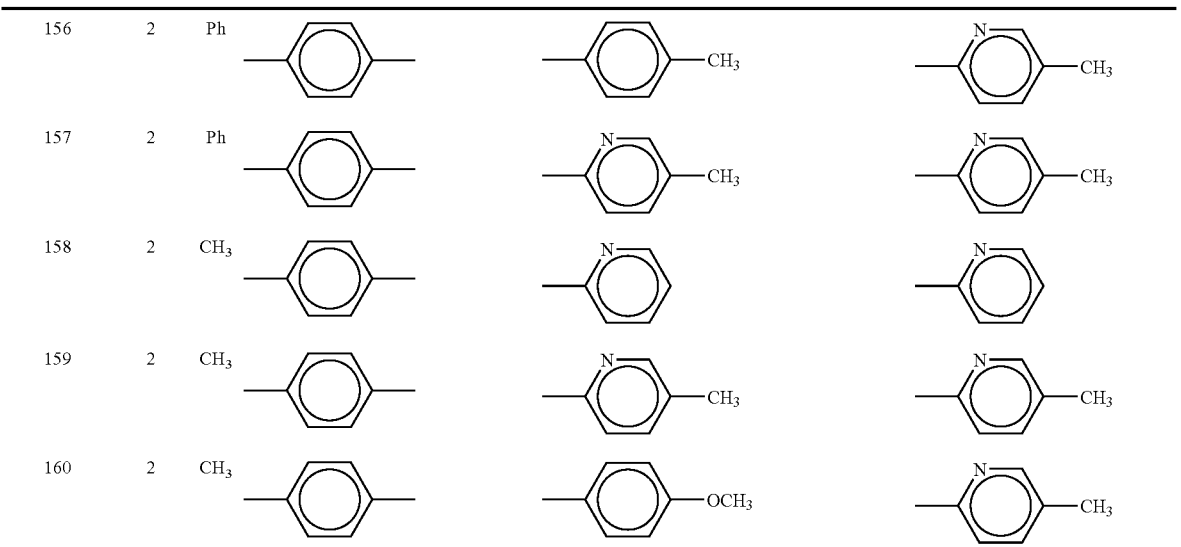

The electroluminescent device in accordance with the present invention comprises a pair of electrodes and an organic layer composed of the silicon compound represented by the formula (1) displaced between the electrodes. The silicon compound is formed between the positive and negative electrodes by a vacuum deposition or solution coating process. The thickness of the organic layer is preferably 2 µm or less, more preferably 0.5 µm or less, and most preferably 0.05 µm to 0.5 µm.

In the electroluminescent device in accordance with the present invention, a plurality of layers may be provided between the two electrodes. In this case, at least one layer among these layers is composed of the compound represented by the formula (1). The luminescent color of the electroluminescent device can be determined by selecting the compound represented by the formula (1).

The electroluminescent device in accordance with the present invention will now be described in detail with reference to the drawings.

FIG. 1 is a schematic cross-sectional view of an embodiment of the electroluminescent device in accordance with the present invention. A positive electrode 2, a luminescent layer 3 and a negative electrode 4 are formed on a substrate 1 in that order. The luminescent layer 3 may be composed of a single compound having hole transportability, electron transportability and luminescence, or a mixture of compounds each having one of these properties.

Figure 2:
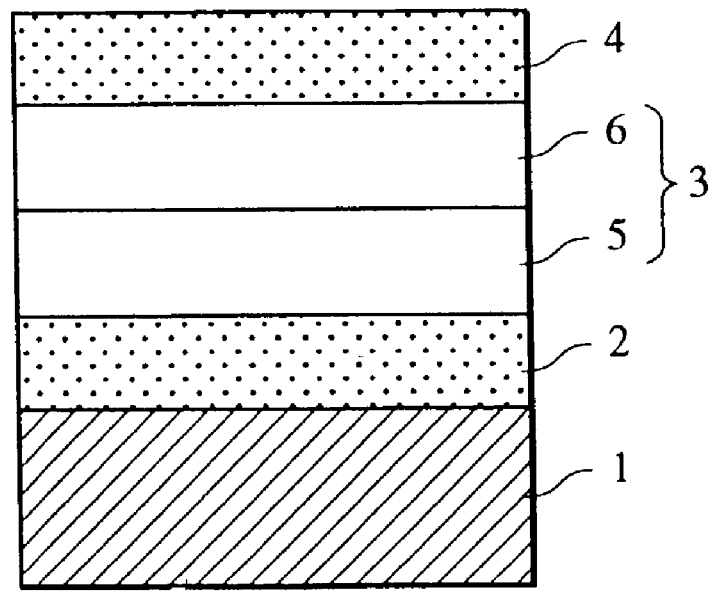
FIG. 2 is a schematic view of an embodiment of an electroluminescent device in accordance with the present invention.

FIG. 2 is a schematic cross-sectional view of another embodiment of the electroluminescent device in accordance with the present invention. A positive electrode 2, a hole transport layer 5, an electron transport layer 6 and a negative electrode 4 are formed on a substrate 1 in that order. The hole transport layer 5 and the electron transport layer 6 form a luminescent layer 3. The hole transport layer 5 may be composed of a luminescent material having hole transportability or a mixture including such a material and a non-luminescent material having hole transportability. The luminescent and non-luminescent materials may also have electron transportability. The electron transport layer 6 may be composed of a luminescent material having electron transportability or a mixture including such a material and a non-luminescent material having electron transportability. The luminescent and non-luminescent materials may also have hole transportability.

Figure 3:
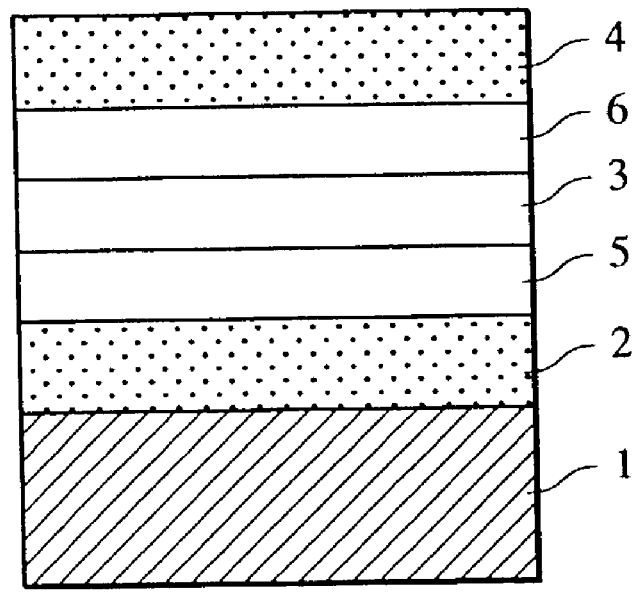
FIG. 3 is a schematic view of an embodiment of an electroluminescent device in accordance with the present invention.

FIG. 3 is a schematic cross-sectional view of a further embodiment of the electroluminescent device in accordance with the present invention. A positive electrode 2, a hole transport layer 5, a luminescent layer 3, an electron transport layer 6 and a negative electrode 4 are formed on a substrate 1 in that order. In this configuration, carrier transport and luminescence are performed in the individual layers. Such a configuration permits a wide variety of combinations of a material having excellent hole transportability, a material having excellent electron transportability and a material having excellent luminescence. Further, the configuration permits the use of various compounds emitting light with different wavelengths; hence the hue of the luminescent light can be controlled within a wide range. Trapping effectively holes and electrons (or excimers) in the central luminescent layer will increase the luminescent efficiency.

Figure 4:
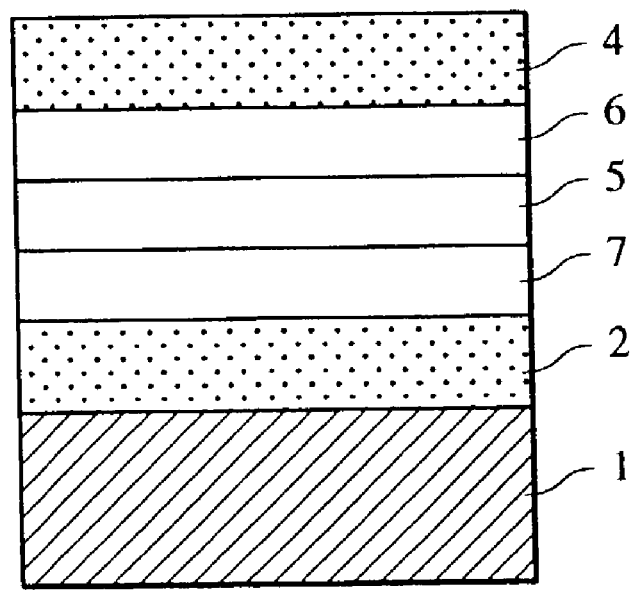
FIG. 4 is a schematic view of an embodiment of an electroluminescent device in accordance with the present invention.

FIG. 4 is a schematic cross-sectional view of a still further embodiment of the electroluminescent device in accordance with the present invention. A positive electrode 2, a hole injection/transport layer 7, a hole transport layer 5, an electron transport layer 6 and a negative electrode 4 are formed on a substrate 1 in that order.

The silicon compound in accordance with the present invention represented by the formula (1) has excellent luminescence compared to known compounds, and can be used for the electroluminescent devices shown in FIGS. 1 to 4.

The silicon compound represented by the formula (1) has hole transportability and/or carrier transportability depending on the types of the substituent groups. A silicon compound or a combination of different silicon compounds may be used in the configurations shown in FIGS. 1 to 4. In the present invention, another layer or other layers can be provided in addition to at least one silicon compound layer.

The silicon compound represented by the formula (1) is used as a constituent in the luminescent layer or a charge transport layer. These layers may further include various compounds used in electrophotographic photosensitive members. Examples of the compounds include hole transport materials, luminescent hole transport materials (for example, compounds shown in Tables 1 to 5), electron transport materials, and luminescent electron transport materials (for example, compounds shown in Tables 6 to 9).

Table 10 illustrates examples of dopant dyes. The addition of a trace amount of dopant dye in the luminescent layer will significantly increase the luminescent efficiency or will change the luminescent color.

TABLE 1

Hole Transport Compound

[chemical structures]

TABLE 1-continued

Hole Transport Compound

[chemical structures]

TABLE 2

Hole Transport Compound

[chemical structures]

TABLE 2-continued
Hole Transport Compound
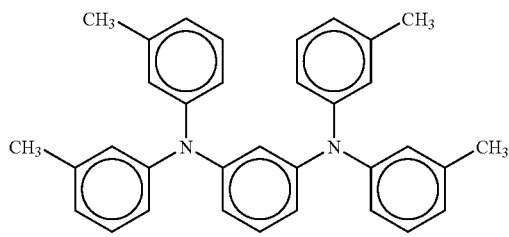
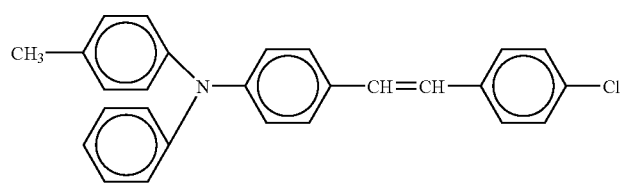
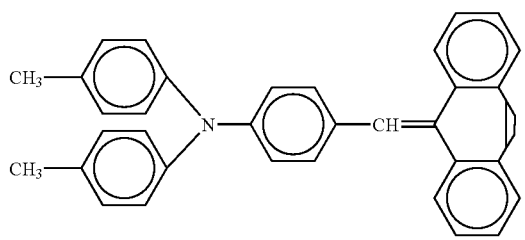
TABLE 3
Hole Transport Compound
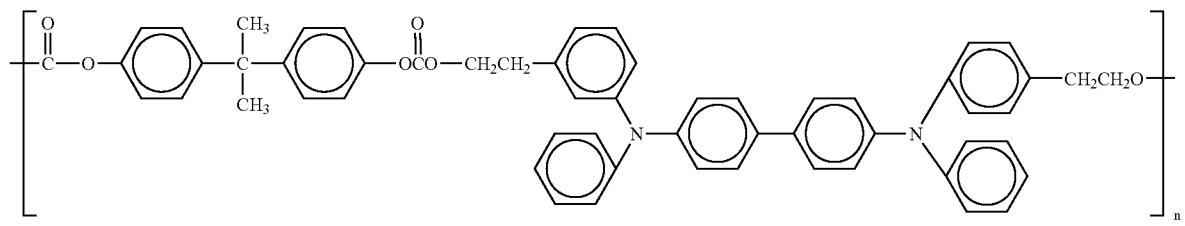
| TABLE 4 | TABLE 4-continued |
|---|---|
| Hole Transport Compound | Hole Transport Compound |
| 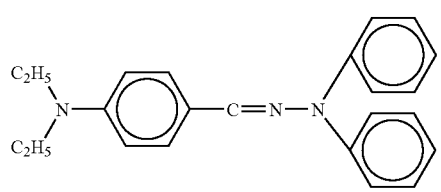 | 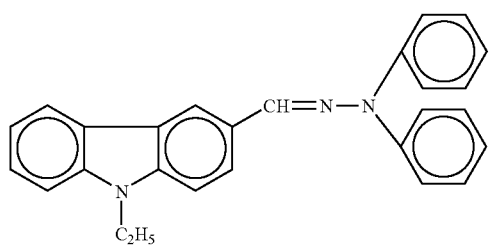 |

TABLE 4-continued
Hole Transport Compound
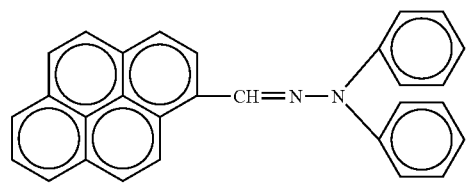
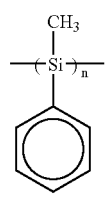
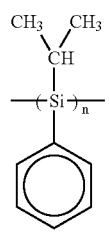
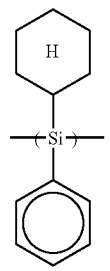
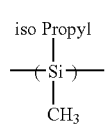
TABLE 5
Hole Transport Compound
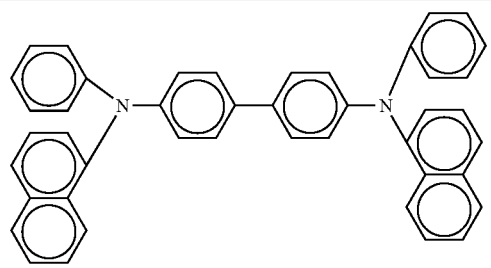
TABLE 5-continued
Hole Transport Compound
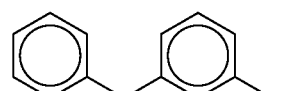
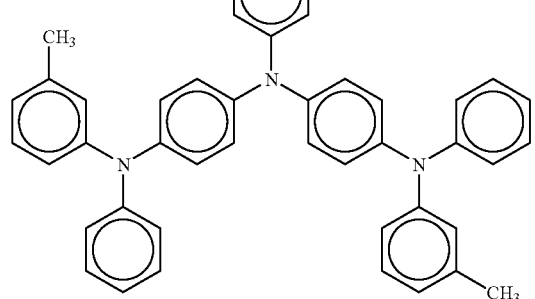
TABLE 6
Electron Transport Compound
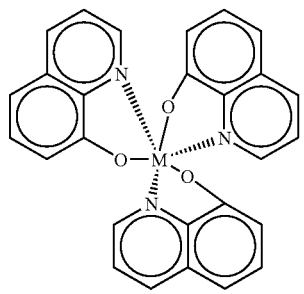
M: Al, Ga
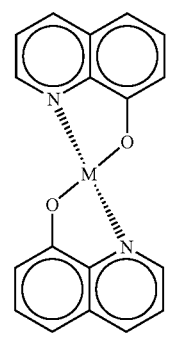
M: Zn, Mg, Be TABLE 6-continued
Electron Transport Compound
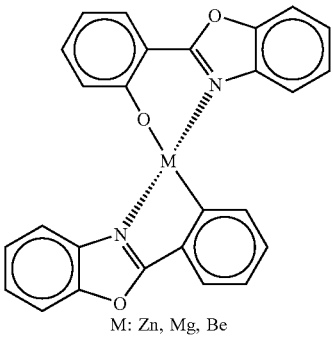
M: Zn, Mg, Be
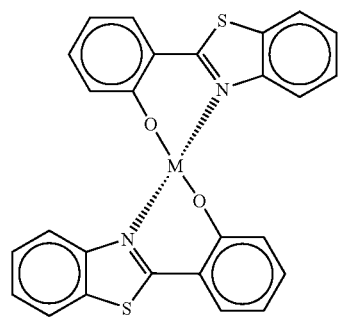
M: Zn, Mg, Be
TABLE 8
Electron Transport Compound
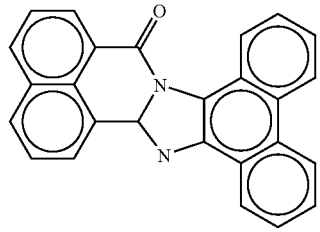
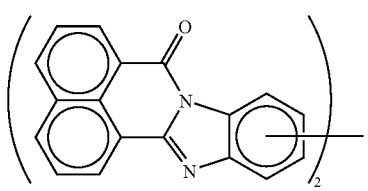
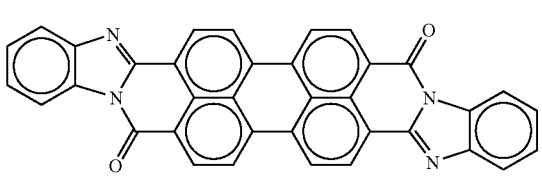
TABLE 7
Electron Transport Compound
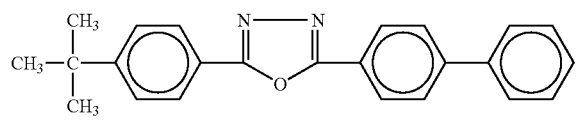
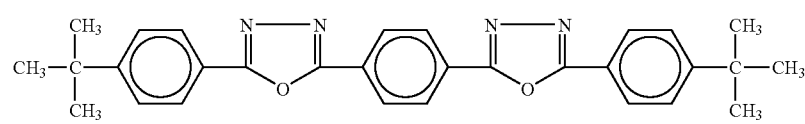
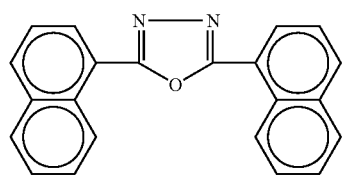
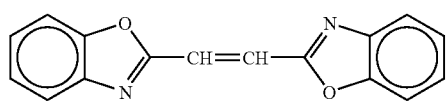

TABLE 8-continued
| Electron Transport Compound | |
|---|---|
| 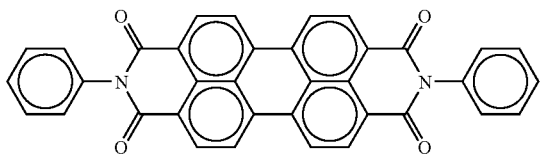 | 5 |
| | 10 |
TABLE 9
| Electron Transport Compound |
|---|
| 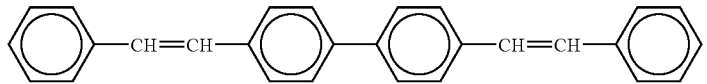 |
| 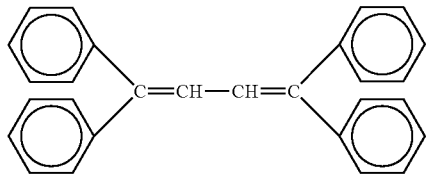 |
| 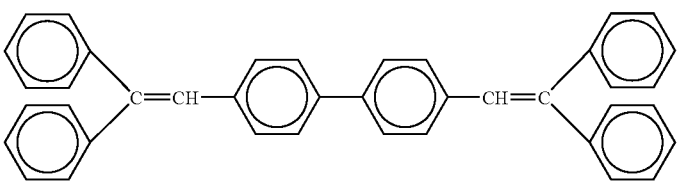 |
| 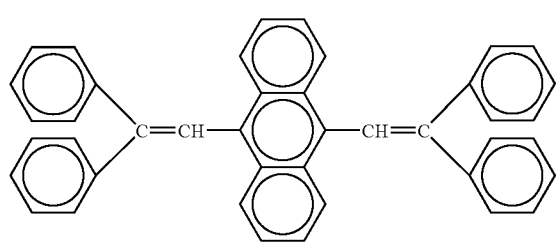 |
| 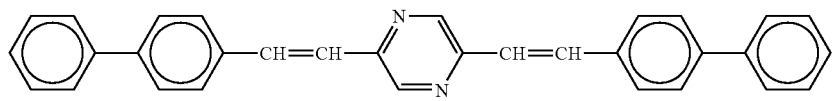 |
| 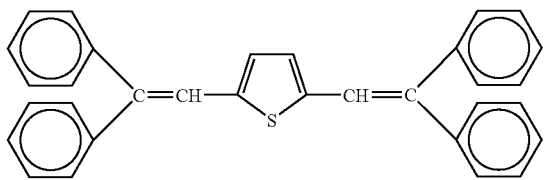 |

TABLE 10

Dopant Dye

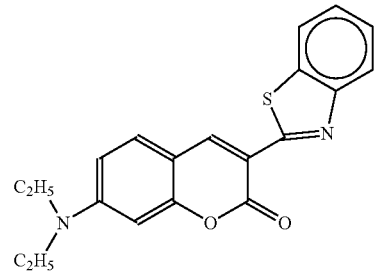

In the electroluminescent device in accordance with the present invention, each layer on the substrate is formed by a vacuum deposition process or a coating process using a combination of the relevant compound and a suitable binding resin.

Non-limiting examples of the binding resins include polyvinyl carbazole resins, polycarbonate resins, polyester resins, polyarylate resins, butyral resins, polystyrene resins, polyvinyl acetal resins, diallyl phthalate resins, acrylate resins, methacrylate resins, phenol resins, epoxy resins, silicon resins, polysulfone resins, and urea resins.

These binding resins can be used alone or in combination.

Materials for the positive electrode have preferably large work functions. Examples of preferred materials include nickel, gold, platinum, palladium, selenium, rhenium, and iridium, alloys thereof, tin oxide, indium tin oxide (ITO), and copper iodide. Also, conductive polymers, such as poly(3-methylthiophene), polyphenylene sulfide and polypyrrole, can be used.

Preferred materials for the negative electrode have small work functions. Examples of such materials include silver, lead, tin, magnesium, aluminum, calcium, manganese, indium and chromium, and alloys thereof.

It is preferable that at least one of the materials for the positive and negative electrodes has a transmittance of at least 50% at the wavelength range of the light emerging from the electroluminescent device.

Examples of transparent substrates used in the present invention include glass plates and plastic films.

Since the silicon compound in accordance with the present invention represented by the formula (1) has excellent hole transportability and can form a uniform and smooth film, it is suitable for a hole transport material in an organic EL device.

EXAMPLES

The present invention is described in further detail with reference to the following examples.

Example 1

Synthesis of Compound 2

Five grams of polymethylsilane was dissolved into 50 ml of dried tetrahydrofuran (THF), 0.05 g of platinum chloride acid hydrate and 0.5 g of 4-vinylterphenyl were added, and the THF solution was stirred at room temperature (25° C.) for 10 hours. After the THF solution was concentrated by evacuation, it was placed into 100 ml of methanol. A white precipitate (5.1 g; yield: 92.7%) was obtained. The product (Compound 2) had a weight average molecular weight of 7,000 according to a styrene calibration curve after gel permeation chromatography (GPC).

Example 2

Synthesis of Compound 139

Figure 5:
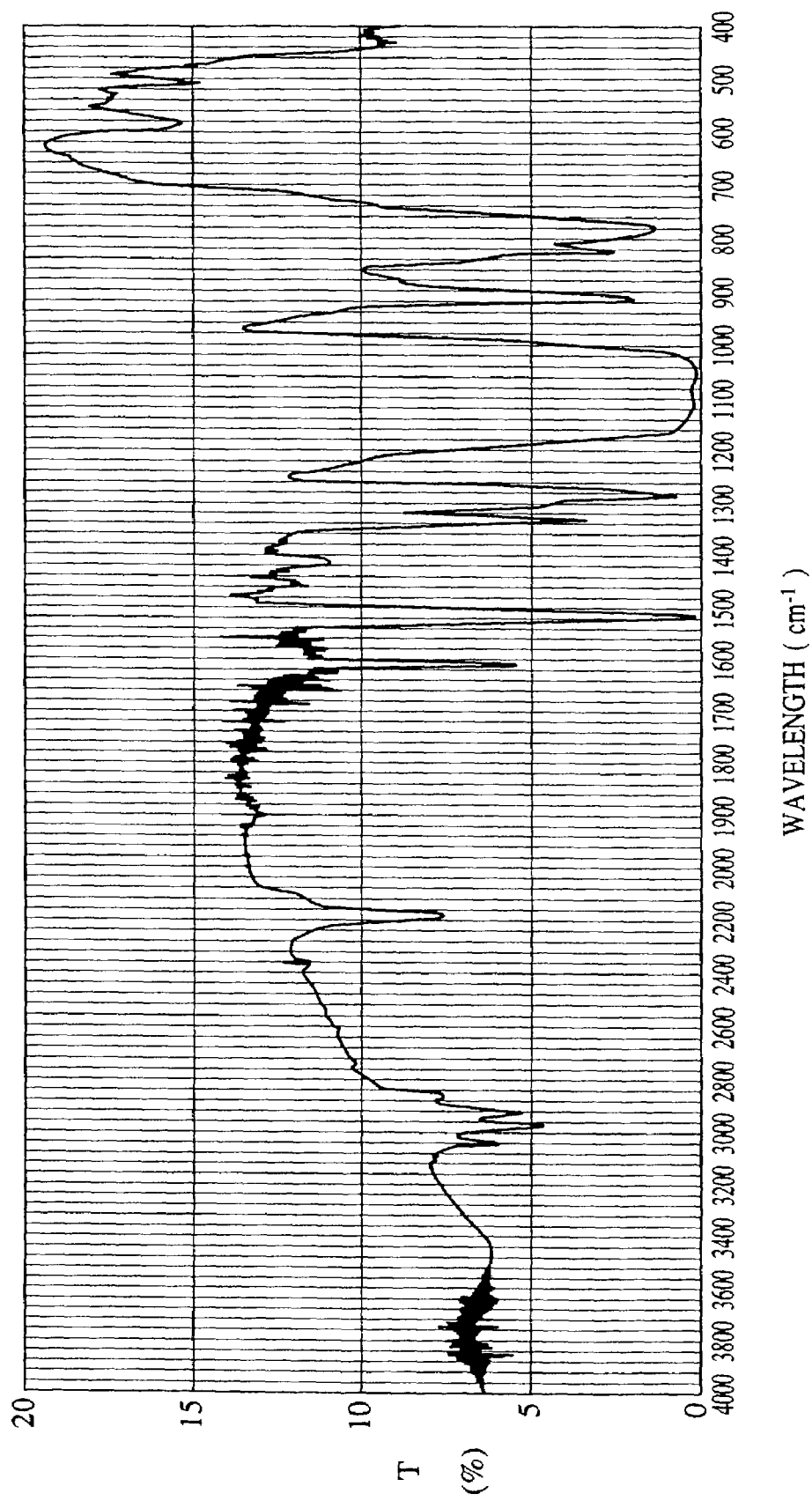
FIG. 5 is an IR spectrum of Compound 19 synthesized in Example 1 in accordance with the present invention.

Five grams of polymethylsilane was dissolved into 50 ml of dried THF, 0.05 g of platinum chloride acid-hydrate and 0.5 g of N,N-(p-ditolylamino)styrene were added, and the THF solution was stirred at room temperature (25° C.) for 10 hours. After the THF solution was concentrated by evacuation, it was placed into 100 ml of methanol. A white precipitate (4.8 g; yield: 87%) was obtained. The product had a weight average molecular weight of 3,500 according to the styrene calibration curve after gel permeation chromatography (GPC). FIG. 5 is an infrared spectrum of the resulting Compound 139.

Example 3

Synthesis of Compound 145

Five grams of polymethylsilane was dissolved into 50 ml of dried THF, 0.05 g of platinum chloride acid hydrate and 0.5 g of N,N-p-ditolyl(p-allylphenyl)amine were added, and the THF solution was stirred at room temperature (25° C.) for 10 hours. After the THF solution was concentrated by evacuation, it was placed into 100 ml of methanol. A white precipitate (4.8 g; yield: 78%) was obtained. The product (Compound 145) had a weight average molecular weight of 3,000 according to the styrene calibration curve after gel permeation chromatography (GPC).

Example 4

Measurement of Hole Mobility

Of each of the polysilane compounds (Compounds 139 and 145) of Examples 2 and 3, 2.5 g was dissolved into 10 ml of toluene. The solution was applied by a Meyer bar onto an aluminum substrate provided with a titanium oxyphthalocyanine layer with a thickness of 1,000 Å, which was deposited by a vacuum deposition process, to form a coating layer having a thickness of 15 μm. The hole mobility in the sample was determined by a xerographic time-of-flight method. The results are as follows:

$\mu d = 3.5 \times 10^{-4}$ cm$^2$/V·sec     Compound 139:

$\mu d = 2.3 \times 10^{-4}$ cm$^2$/V·sec     Compound 145:

Both coating layers were satisfactorily formed and did not have any cracks.

Comparative Example 1

A film was formed as in Example 4, but the following compound was used instead of Compound 139 or 145.

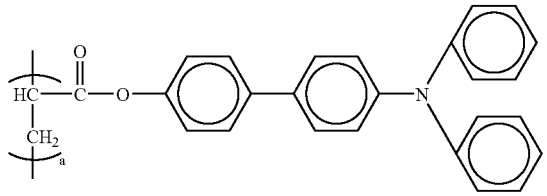

The hole mobility of the sample is as follows:

$\mu d = 3.5 \times 10^{-4}$ cm$^2$/V·sec

The coating layer had some cracks and a rough surface.

Example 5

An indium tin oxide (ITO) layer with a thickness of 100 nm was deposited on a glass plate by a sputtering process, and the resulting transparent substrate was cleaned with deionized water and isopropyl alcohol. Next, 0.20 g of Compound 8 was dissolved into 10 ml of THF to prepare a coating solution, and then the coating solution was applied onto the transparent substrate by a spin coating process to form a coating layer with a thickness of 110 nm. An aluminum electrode with a thickness of 200 nm was deposited by a vacuum deposition process to form a device having the configuration shown in FIG. 1.

A direct current of 10 V was applied between the ITO positive electrode and the Al negative electrode. A current flow of 12 mA/cm$^2$ and a blue luminescence with a luminance of 200 cd/m$^2$ were observed.

Comparative Example 2

A transparent glass substrate provided with an ITO layer having a thickness of 100 nm deposited by a sputtering process was cleaned with deionized water and isopropyl alcohol. Next, 0.20 g of methylphenylpolysilane (weight average molecular weight: 30,000) was dissolved into 10 ml of THF to prepare a coating solution. The coating solution was applied onto the transparent substrate by a dip coating process to form a coating layer with a thickness of 110 nm. An aluminum electrode with a thickness of 200 nm was deposited thereon by a vacuum deposition process to form a device having the configuration shown in FIG. 1.

A direct current of 12 V was applied between the ITO positive electrode and the Al negative electrode. A current flow of 0.150 mA/cm$^2$ and no luminescence were observed.

Example 6

A transparent glass substrate provided with an ITO layer having a thickness of 100 nm deposited by a sputtering process was cleaned with deionized water and isopropyl alcohol. Next, 0.50 g of Compound 61 was dissolved into 25 ml of THF to prepare a coating solution. The coating solution was applied onto the transparent substrate by a dip coating process to form a coating layer with a thickness of 60 nm as a hole transport layer. An aluminum quinolinol layer with a thickness of 50 nm as an electron transport layer was deposited thereon by a vacuum deposition process. A metallic electrode having a composition of Mg:Ag=10:1 by atomic ratio was deposited thereon by a vacuum deposition process to form a device having the configuration shown in FIG. 2.

A direct current of 7 V was applied between the ITO positive electrode and the Mg/Ag negative electrode. A current flow of 11 mA/cm$^2$ and a green luminescence having a luminance of 265 cd/m$^2$ were observed. A voltage with a current density of 10 mA/cm$^2$ was applied to the sample for 2,000 hours. The luminance was 250 cd/m$^2$ at the start and changed to 225 cd/m$^2$ at the end.

Example 7

A transparent glass substrate provided with an ITO layer having a thickness of 100 nm deposited by a sputtering process was cleaned with deionized water and isopropyl alcohol. Next, 0.20 g of vinylcarbazole was dissolved into 15 ml of THF to prepare a coating solution. The coating solution was applied onto the transparent substrate by a spin coating process to form a coating layer with a thickness of 40 nm as a hole transport layer. A coating solution containing 0.20 g of Compound 100 in 20 ml of THF was applied thereon by a spin coating process to form a luminescent layer with a thickness of 15 nm. An aluminum quinolinol layer with a thickness of 50 nm as an electron transport layer was deposited thereon by a vacuum deposition process. A metallic electrode having a composition of Al:Li=97:3 by atomic ratio was deposited thereon by a vacuum deposition process to form a device having the configuration shown in FIG. 3.

A direct current of 12 V was applied between the ITO positive electrode and the Al/Li negative electrode. A current flow of 25 mA/cm$^2$ and a green luminescence having a luminance of 330 cd/m$^2$ were observed. A voltage with a current density of 15 mA/cm$^2$ was applied to the sample for 2,000 hours. The luminance was 250 cd/m$^2$ at the start and changed to 213 cd/m$^2$ at the end.

Example 8

A transparent glass substrate provided with an ITO layer having a thickness of 100 nm deposited by a sputtering process was cleaned with deionized water and isopropyl alcohol. Next, 0.20 g of Compound 88 was dissolved into 15 ml of THF to prepare a coating solution. The coating solution was applied onto the transparent substrate by a spin coating process to form a coating layer with a thickness of 30 nm as a hole injection/transport layer. A hole transport layer with a thickness of 20 nm composed of α-NPD (N,N'-Diphenyl-N,N'-di(naphthyl)-4,4'-diamino-biphenyl) represented by the formula (5) and an electron transport layer with a thickness of 50 nm composed of an aluminum quinolinol layer were deposited thereon by a vacuum deposition process in that order. An aluminum electrode was deposited thereon by a vacuum deposition process to form a device having the configuration shown in FIG. 4.

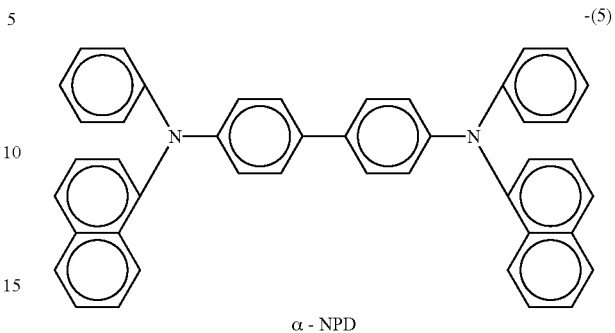

α - NPD

A direct current of 10 V was applied between the ITO positive electrode and the Al negative electrode. A current flow of 21 mA/cm$^2$ and a green luminescence having a luminance of 425 cd/m$^2$ were observed. A voltage with a current density of 11 mA/cm$^2$ was applied to the sample for 2,000 hours. The luminance was 250 cd/m$^2$ at the start and changed to 230 cd/m$^2$ at the end.

Example 9

A transparent glass substrate provided with an ITO layer having a thickness of 100 nm deposited by a sputtering process was cleaned with deionized water and isopropyl alcohol. Next, 0.50 g of Compound 139 was dissolved into 25 ml of THF to prepare a coating solution. The coating solution was applied onto the transparent substrate by a dip coating process to form a coating layer with a thickness of 60 nm as a hole transport layer. An aluminum quinolinol layer with a thickness of 50 nm as an electron transport layer was deposited thereon by a vacuum deposition process. A metallic electrode having a composition of Mg:Ag=10:1 by atomic ratio was deposited thereon by a vacuum deposition process to form a device having the configuration shown in FIG. 2.

A direct current of 8 V was applied between the ITO positive electrode and the Mg/Ag negative electrode. A current flow of 13 mA/cm$^2$ and a green luminescence having a luminance of 470 cd/m$^2$ were observed. A voltage with a current density of 5 mA/cm$^2$ was applied to the sample for 2,000 hours. The luminance was 250 cd/m$^2$ at the start and changed to 220 cd/m$^2$ at the end.

Example 10

An ITO layer with a thickness of 100 nm was deposited on a glass plate by a sputtering process, and the resulting transparent substrate was cleaned with deionized water and isopropyl alcohol. Next, 0.20 g of Compound 104 was dissolved into 10 ml of THF to prepare a coating solution, and then the coating solution was applied onto the transparent substrate by a spin coating process to form a coating layer with a thickness of 100 nm. An aluminum electrode with a thickness of 200 nm was deposited thereon by a vacuum deposition process to form a device having the configuration shown in FIG. 1.

A direct current of 12 V was applied between the ITO positive electrode and the Al negative electrode. A current flow of 15 mA/cm$^2$ and a red luminescence with a luminance of 210 cd/m$^2$ were observed.

While the present invention has been described with reference to what are presently considered that the invention is not limited to the disclosed embodiments. To the contrary, the invention is intended to cover various modifications and equivalent arrangements, included within the spirit and scope of the appended claims. The scope of the following claims is to be accorded the broadest interpretation so as to encompass all such modifications and equivalent structures and functions.

What is claimed is:

1. A method for synthesizing of a silicon compound having a single, identical repeating unit represented by the following general formula (1) comprising reacting a compound represented by the general formula (2) with a compound represented by the general formula (3):

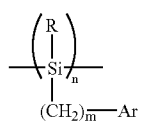

wherein R is a hydrogen atom, a straight or branched alkyl group having 1 to 20 carbon atoms, a substituted or unsubstituted aryl group, or a substituted or unsubstituted heterocyclic group, Ar is a substituted or unsubstituted polyaryl group or an unsubstituted heterocylic group, m is an integer of 2 or more, and n is an integer where $2 \leq n \leq 5{,}000$;

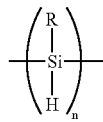

wherein R is a hydrogen atom, a straight or branched alkyl group having 1 to 20 carbon atoms, a substituted or unsubstituted aryl group, or a substituted or unsubstituted heterocyclic group, and n is an integer where $2 \leq n \leq 5{,}000$:

$$CH_2=CH-(CH_2)_{m-2}-Ar \quad (3)$$

wherein Ar is a substituted or unsubstituted polyaryl group or an unsubstituted heterocyclic group, and m is an integer of 2 or more, wherein n in the general formula (1) and n in the general formula (2) are the same.

2. A method for synthesizing of a silicon compound according to claim 1, wherein the reaction is performed in the presence of a catalyst.

3. A method for synthesizing of a silicon compound according to claim 2, wherein said catalyst is platinum chloride acid hydrate.

4. A method for synthesizing of a silicon compound according to claim 1, wherein said Ar is a π-conjugated hydrocarbon group having 12 or more carbon atoms.

5. A method for synthesizing of a silicon compound according to claim 4, wherein said π-conjugated hydrocarbon group is a polyphenylene group.

6. A method for synthesizing of a silicon compound according to claim 4, wherein said π-conjugated hydrocarbon group is a stilbene group.

7. A method for synthesizing of a silicon compound according to claim 1, wherein said Ar is a fused-ring polycyclic group or a fused-ring poly/heterocyclic group.

8. A method for synthesizing of a silicon compound according to claim 1, wherein said Ar is a heterocyclic group.

9. A method for synthesizing of a silicon compound according to claim 8, wherein said heterocyclic group is a polyheterocyclic group.

10. A method for synthesizing of a silicon compound according to claim 1, wherein said Ar is a moiety of a tertiary amine.

11. A method for synthesizing of a silicon compound according to claim 10, wherein said moiety of the tertiary amine is represented by the general formula (4):

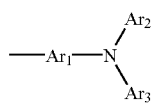

wherein $Ar_1$ represents a substituted or unsubstituted arylene group or a substituted or unsubstituted divalent heterocyclic group, and $Ar_2$ and $Ar_3$ each represents a substituted or unsubstituted aryl group or a substituted or unsubstituted heterocyclic group.

12. A method for synthesizing of a silicon compound according to claim 10, wherein said $Ar_1$ is a substituted or unsubstituted arylene group selected from the group consisting of a phenylene group, a biphenylene group, and a naphthylene group.

13. A method for synthesizing of a silicon compound according to claim 10, wherein said $Ar_1$ is a substituted or unsubstituted divalent heterocyclic group selected from the group consisting of a pyridine group, a furyl group, and a thiophene group.

14. A method for synthesizing of a silicon compound according to claim 10, wherein said unsubstituted aryl group of said $Ar_2$ and $Ar_3$ is a polycyclic aryl group.

15. A method for synthesizing of a silicon compound according to claim 10, wherein said unsubstituted aryl group of said $Ar_2$ and $Ar_3$ is a fused-ring aryl group.

16. A method for synthesizing of a silicon compound according to claim 10, wherein said unsubstituted heterocyclic group of said $Ar_2$ and $Ar_3$ is a 6-member ring or a 5-member ring.

17. A method for synthesizing of a silicon compound according to claim 10, wherein said unsubstituted heterocyclic group of said $Ar_2$ and $Ar_3$ is a fused-ring heterocyclic group.

18. A method for synthesizing of a silicon compound according to claim 10, wherein said substituted aryl group or said substituted heterocyclic group has said substituent selected from the group consisting of halogen, alkyl, methoxy, alkoxy, aryloxy, amino, nitro, aryl, aralkyl, and alkenyl.

* * * * *